United States Patent [19]

Armand et al.

[11] 4,359,327

[45] Nov. 16, 1982

[54] GAS ADSORPTION AGENTS PARTICULARLY FOR SEPARATING $H_2$ FROM A GASEOUS PHASE

[75] Inventors: Michel B. Armand, Annecy; Francis J. P. Jeanne, Saint-Ismier, both of France

[73] Assignee: Agence Nationale de Valorisation de la Recherche, Neuilly sur Seine, France

[21] Appl. No.: 153,865

[22] Filed: May 28, 1980

[30] Foreign Application Priority Data

May 29, 1979 [FR] France .................................. 79 13697

[51] Int. Cl.³ ........................ B01D 53/04; B01D 59/14
[52] U.S. Cl. ........................................... 55/16; 55/35; 55/68; 55/74; 585/426; 429/17; 429/42
[58] Field of Search .................. 55/74, 16, 35, 68; 260/465 R; 526/252; 528/362, 397; 570/138, 184, 191; 585/24, 426, 436; 429/17, 42

[56] References Cited

U.S. PATENT DOCUMENTS

| | | | |
|---|---|---|---|
| 3,164,625 | 1/1965 | Pollart | 528/362 X |
| 3,198,844 | 8/1965 | Errede | 585/25 |
| 3,221,068 | 11/1965 | Gorham | 528/397 X |
| 3,342,754 | 9/1967 | Gorham | 528/397 X |
| 3,692,784 | 9/1972 | Lindberg | 585/24 X |
| 3,754,015 | 8/1973 | Hedaya | 585/426 X |
| 3,917,469 | 11/1975 | Cotter et al. | 55/74 X |
| 4,003,257 | 1/1977 | Fletcher et al. | 55/74 X |

OTHER PUBLICATIONS

Cram et al., Macro Rings, XIX, Olefinic Paracyclophanes, J.A.C.S., 1959–1981, pp. 5963–5971.

*Primary Examiner*—Robert H. Spitzer
*Attorney, Agent, or Firm*—Omri M. Behr

[57] ABSTRACT

Gas adsorbents comprise at least one paracyclophane (or PCP) derivative, constituted by cyclic oligomers formed of mer-units which are interlinked so as to define a rigid structure with a substantially cylindrical intramolecular cavity. The dimensions of the cross-section of said cavity correspond substantially to those of the one or more types of gas molecules that it is desired to introduce therein.

24 Claims, No Drawings

GAS ADSORPTION AGENTS PARTICULARLY FOR SEPARATING H₂ FROM A GASEOUS PHASE

The invention relates to novel gas adsorption agents particularly useful for separating gases from a given medium, more especially for their concentration and/or their storage.

It relates more particularly, due to the interest of their application in many fields, to adsorbents which can store hydrogen molecules selectively.

It is known that the hydrogen molecule is of little reactivity which makes its retention in a given system difficult.

It has been proposed to store hydrogen in the form of a hydride by causing it to react with a metal such as magnesium or an alloy such as $LaNi_5$ or of the Fe-Ti type.

The synthesis of such hydrides always necessitates, disadvantageously, the utilisation of high temperatures, for example, of the order of 350° C. to form magnesium hydride $MgH_2$.

In addition, such a synthesis involves the dissociation of the hydrogen molecule and therefore presents the drawback of a relatively long reaction kinetics.

Studies have also been made on encapsulation systems enabling the hydrogen to be trapped in a crystalline lattice without dissociation of the molecule occuring. Thus the possibility is known of trapping hydrogen in a zeolite or in a particular clathrate (mixed hydrate with chloroform). However, these compounds have a very low storage capacity for hydrogen near ambient temperature, which restricts their field of application.

It is an object of the invention to realize the non-dissociative inclusion of hydrogen, and the research carried out has enabled it to be shown that by selecting a certain type of organic compound corresponding to a definite molecular structure, systems can be obtained capable of retaining satisfactorily, from ambient temperature, gas molecules, particularly hydrogen, and if necessary, more bulky molecules such as oxygen or nitrogen.

It is an object of the invention also to provide novel gas adsorbents in molecular form and more especially those capable of storing hydrogen.

It is a further object of the invention to provide useful forms of these adsorbents notably in a dispersed phase in solution or in a solid state.

According to another aspect of the invention, there are provided novel processes using the novel adsorbents in technical fields where the separation more especially of hydrogen for its concentration and its storage is sought.

The novel adsorbents of the invention include at least one compound belonging to the series of paracyclophanes, or PCP, that is to say compounds constituted by aromatic rings connected in the para position by linear links.

The PCP's used according to the invention are constituted by cyclic oligomers formed from mer-units or repeat-units which link together so as to define a rigid structure with a substantially cylindrical intramolecular cavity, the dimensions of the cross-section of said cavity corresponding substantially to those of the one or more types of gas molecule that it is desired to introduce; the rigidity of said structure being such that the rotary movement of the atoms which constitute said units cannot result in substantial volume variations of the said cavity up to a temperature of the order of 250° C.

The dimensions of the intramolecular cavity, its good geometric adaptation to the molecule that it is desired to include as well as the rigid character of the macrocycle may advantageously be evaluated by using precision molecular models of the CPK type (Corey-Pauling-Koltun).

In practice, those macrocyclic molecules are qualified as "rigid" whose intramolecular cavity does not undergo, through rotary movements of thermal origin at the level of the covalent bonds which form the cyclic structure, more than limited dimensional deformations such that the accessibility of the molecules to be included may be preserved.

Advantageously, the rigidity of the structure is such that the variations in the cross-section of the cavity are at the most equal to about 10% excess or lack up to the above-indicated temperature.

To provide a particularly suitable rigid structure for the retention of hydrogen, recourse is had to PCP trimers, that is to say PCP's whose basic skeleton is formed from 3 units, these units, which can differ from one another, corresponding to the formula RX, in which R is an aromatic cyclic compound with 6 links, substituted at each of the para positions by X, this cylic compound being selected from among the phenylene —$C_6H_4$— radical, or a pyridinyl or pyrimidyl nitrogen aromatic radical, provided that the one or more nitrogen atoms do not occupy the positions substituted at para by X; and X is a linear link with two elements, selected more especially from among the radical:

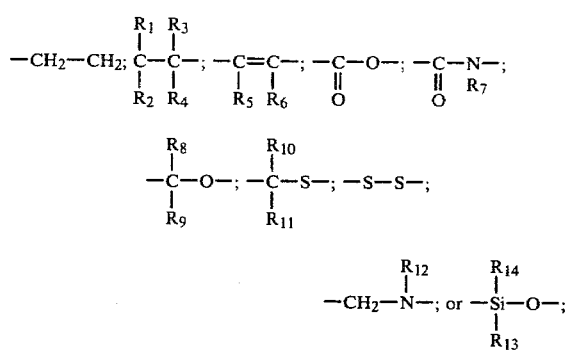

$R_1$ to $R_4$, identical or different from one another, representing a $C_nH_{2n+1}$ group with $0 \leq n \leq 4$ or a halogen atom selected from among F, Cl or Br, $R_5$ to $R_{14}$ being able to represent, in addition to the meanings given for $R_1$ to $R_4$, a hydrogen atom.

In the above-defined trimers, the link chains connecting the aromatic rings are chains with two elements at the para position. This arrangement enables the holding of the rings at a pre-determined distance and at predetermined angles from one another and thus, the obtaining of a stable structure possessing satisfactory rigidity.

The importance of the nature of the link chains described above must be also appreciated at the level of the size of the cavity that they contributed to defining. In controlling such parameters, it is possible to optimise the gas-lattice interactions which is particularly valuable in the case of $H_2$ whose low reactivity has already been stressed.

It will be noted in this respect that in the above-defined trimers, the inner diameter of the cavity is of the order of 1.8 to 2.6 A, for example 2 A when X represents the group —CH₂—CH₂, whilst the hydrogen molecule is an ellipsoid with a=b=2.1 A and c=3 A.

It is clear that the volumic space of the PCP's can be increased by using a link including sulfur or a siloxane or alkene group. This being the case, the choice of a given link is a function also of the type of properties that it is desired to confer on the PCP molecule. Also, a link chain substituted in particular by alkyl groups will facilitate notably the lowering of the melting point of the products. To increase, notably, the solubility of the PCP's in alcoholic or chlorinated solvents, it is advantageous to select link chains of the ester type. The siloxane link for itself enables in particular the stability of the basic molecule to be increased.

The nature of the aromatic ring R must also be taken into consideration and thus a nitrogen aromatic ring is more particularly used when it is desired to have adsorbents with increased solubility notably in water.

Paracyclophanes corresponding to the general characteristics defined above, but which possess intramolecular housing of a size greater than that of the trimers concerned and appear hence more suitable for the introduction of gas molecules more bulky than H₂ such as O₂ or N₂ include at least one cyclic tetramer formed from mer-units R-Y in which R has the meaning already given and Y is a link chain with an element selected from the group consisting of

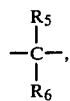

in which R₅ and R₆ have the above-indicated meanings;

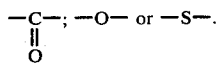

In certain embodiments of the invention, the above-defined cyclic oligomers include one or several substituents M on the aromatic rings, these substituents being selected from among those whose bulk does not interfere with access to the inner cavity of the molecule.

A suitable choice for the substituents M enables also the rigid character of the cavity to be increased by reinforcing the rotation barriers.

The choice of these substituents is more particularly guided by the type of property that it is desired to improve or confer on the basic molecule.

Thus, in order to improve notably the hydrophobic character of the PCP's used in the invention, halogen substitutions are used.

Fluorinated compounds are found to be particularly satisfactory in this respect, and have, in addition, the advantage of giving PCP's possessing improved thermal stability.

Use of acid groups such as —COOH or —SO₃H enables the obtaining of better solubilisation of the PCP's in an aqueous media. Thus the solubilisation in aqueous media of the PCP's is increased by introducing nitrogenated groups and more especially ammonium cations of the type —N(R₁₅)₃⁺, R₁₅ representing a $C_n$, $H_{2n'+1}$ radical with $0 \leq n' \leq 2$. The substituents M are advantageously present in the proportion of 1 or 2 per molecule of PCP and even up to 4 per aromatic ring in the case more particularly of F.

As the M substituent, there may be advantageously also applied a group capable of reacting easily with other chemical compounds and/or of being polymerised.

An ethylenic unsaturated group such as the vinyl group presents great interest in this respect, taking into account its easy production, by conventional methods.

According to an advantageous aspect of the invention, enabling adsorbents to be provided easily in macromolecular form, which considerably widen their field of application, PCP derivatives attached to a polymer chain are used. This chain can result from the polymerisation of a polymerisable substituent of PCP and correspond for example to a chain of the poly (vinyl) type, if necessary copolymerised with monomers such as vinylidene fluoride or an acetal of vinyl chloride. It is possible also to have derivatives constituted by PCP's grafted to a polymer chain which constitutes in a way a pattern or framework on which the PCP molecules are fixed. Such a chain is, for example, constituted by poly (p-vinyl), p'-methyl-PCP benzene

Generally speaking the representation of a chemical group linkage (PCP) signifies, in the description and the claims, that the chemical group concerned occupies one of the free positions of one of the aromatic rings of the PCP.

The preparation of the above PCP's is carried out by known techniques.

In general, there is applied as starting material, the aromatic derivative including the desired nucleus, substituted at each of the para positions by a functional group suitable for the obtaining of the connecting links desired for the PCP, this nucleus being as necessary substituted at the other free positions of the ring by one of the above-indicated elements M or by a substituent which can lead to such element.

For the synthesis of the PCP trimers in which the aromatic nuclei are joined by ethylene groups, there is made to react for example a para-xylylene halide in the presence of tetra phenylethylene and of sodium in a solvent medium such as tetrahydrofurane.

A preferred modification for the preparation of derivatives of this type is based on the pyrolysis of para-xylene and described by Errede and al in JACS, vol. 82, 5218-23 (1960).

The obtaining of PCP trimers whose nuclei are connected by the above-described functional links involves current laboratory practice for the synthesis of such groups.

As regard the preparation of tetramer PCP's, it is advantageously carried out by a Friedel and Crafts type reaction in the presence of a chlorinated inert solvent.

The synthesis of these trimers or tetramers is generally accompanied by the formation of linear compounds and/or of higher oligomers. The removal of these products is advantageously carried out by column chromatography.

Adsorption on silica gel is generally found to be satisfactory and the desired separation is carried out by means of eluents such as benzene or hexane, if necessary by operating in a concentration gradient.

Study of the behaviour with respect to gases of the PCP's corresponding to the above-defined characteristics has shown that their inner space constitutes a host structure with respect to gas molecules of sizes substantially close to those of the inner space. Trials relating to the adsorption of $H_2$ by cyclic trimers will be more particularly considered below. However it is clear that the cyclic trimers whose inner cavity possesses a greater size enable the retention of molecules whose volume is greater than that of hydrogen and such as those of $O_2$ or $N_2$.

In general, it is observed that hydrogen becomes advantageously housed in the inner cavity of cyclic trimers without dissociation of the molecule, at temperatures close to ambient and by operating within an easily accessible pressure range, of the order of 5 to 100 bars and notably from 5 to 50 bars.

These PCP's are found therefore to be particularly valuable for separating, under easily operational conditions, hydrogen from media including it or to isolate phases including it from other media and this, as soon as the cavity of the PCP's cannot admit more bulky molecules.

By reason of the sifting so obtained, the adsorbents of the invention find applications in many sectors of industry wherein a selective hydrogen separation is sought. The amounts of adsorbents to be applied to obtain the desired efficiency is easily determinable in each case.

These adsorbents are hence used with advantage for increasing the hydrogen contents of a phase as well as for purposes of purification. By enabling the removal of molecules whose volume is greater than that of molecules of hydrogen such as $O_2$, CO or even $H_2O$ which may accompany $H_2$, these adsorbents play the role of material transfer agents, modifying the composition of a given system.

It is also advantageous to apply the adsorbents of the invention as protective agents for hydrogen storage compounds such as metal hydrides. The sifting effect of the trimer adsorbents prevents contact of the hydrides with oxygen and water vapor. They take part also advantageously in the hydrogen retention process.

Their electrochemical applications assume also a great importance.

The adsorbents of the invention are thus useful for the forming of gas electrodes and enable hydrogen to be isolated, contained in any mixture, from an electrolytic medium, for example aqueous.

Such electrodes formed of a porous metal and of conventionally used materials for their manufacture, but including over at least a portion of their surface an adsorbent according to the invention, for example, advantageously in film form, come within the scope of the invention.

The adsorbents of the invention are useful similarly in fuel cells operating, for example, with methanol and giving rise to the formation of carbon monoxide and hydrogen, as well as in electrochemical generators whose operation brings into play an equilibrium with hydrides such as the system $NiO_2H_x$-$H_2$ with $1 < x < 2$ or $Ag O_x$-$H_2$ with $0 < x < 1$. The form of application of the adsorbents depends naturally on the type of application envisaged. It may be desired to use the adsorbents in solid form. Considering however the compact crystalline lattice of the PCP's which constitute them, access to their cavity is then rendered difficult.

It is hence preferable to apply them in dispersed phase.

It may be a dispersion or solution in a liquid and notably in a viscous liquid, more especially, in a conventional membrane material, in proportions enabling the desired adsorptions. In such a form of use the PCP is advantageously grafted to a polymer chain by radiation or by a chemical method, for example, to poly (p-vinyl, p'-chloro-methyl-benzene) or again used in polymer form, for example, polyvinyl (PCP).

It is also advantageous to incorporate them, in an effective amount according to the application envisaged, more especially by copolymerisation in an amorphous dispersed phase of a macromolecular material. Such copolymers are useful in the form of beads or granules, for example, in a separation column or again in the form of membranes or films.

DESCRIPTION OF PREFERRED EMBODIMENTS

Other characteristics and advantages of the invention will appear in the course of the description of the following examples.

EXAMPLE 1

Preparation of tris[2,2,2]paracyclophane or $2^3$PCP of the formula

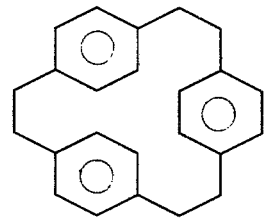

By operating according to the method of Tabushi et al, described in Tetrahedron vol. 27, p 4845-53, the synthesis of $2^3$PCP is carried out by using p-xylylene chloride $ClCH_2$—$C_6H_4$—$CH_2Cl$, tetraphenylethylene $(H_5C_6)_2$—C=C—$(C_6H_5)_2$ and powdered sodium.

10 g of sodium powder is added to a solution of 1 g of tetraphenylethylene in one liter of tetrahydrofurane (THF). The mixture is heated under reflux with vigorous stirring. After development of a violet color in the reaction mixture, 25 g of p-xylylene chloride in 200 ml of anhydrous THF is added. This addition is carried out at a speed enabling the maintenance of the violet color in the reaction mixture, which correspond approximately to a period of 48 hours. The mixture is then filtered and, by evaporating the filtrate, a solid is obtained which is chromatographed on silica gel by using a hexane-benzene elution gradient. The desired $2^3$PCP is recovered with a yield close to 12%. MP: 168° C. (n-hexane).

Physical characteristics:

IR (KBr) cm$^{-1}$: 3020, 2925, 2850, 1515, 1440, 795, 750.

NMR (CCl$_4$, TMS, 33° C.)$\delta CH_2 = 2.93$ (s); $\delta_{arom} = 6.62$ (s).

UV (n-hexane); $\lambda$nm (log $\epsilon$): 276 (2.90); 268 (2.97); 262 (2.85).

MS; m/e: 312 [M$^+$]; 104 ($CH_2$—$C_6H_4$—$CH_2$).

According to another operational method, the synthesis of the $2^3$PCP is carried out by pyrolysing p- xylene in accordance with the Errede et al technique based on the following reaction:

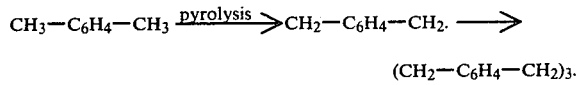

$$(CH_2-C_6H_4-CH_2)_3.$$

An approximately 0.10 molar solution of p-xylylene in hexane is prepared by rapid pyrolysis of p-xylene and condensation of pyrolysate produced in 4 l. of hexane kept at −78° C.

The conditions of the pyrolysis were the following: temperature: 1065°±5° C.; pressure: 4.0±0.1 mm of Hg; residence time: 0.0041±0.003 sec.

The solution was then heated from −78° C. to ambient temperature.

The insoluble precipitate which is formed was removed by filtration and the filtrate was evaporated to dryness. The processing of the filtrate enabled the recovery of 570 g of $2^3$PCP of MP=167° C.

The synthesis of the various substituted PCP's defined above is naturally possible by this method. By way of illustration there are presented below in Example 13 results of tests relating to hydrogen adsorption by $2^3$PCP in dispersed phase in solution.

EXAMPLE 2

Preparation of $2^3$ vinyl-PCP $$CH_2=CH(PCP)$$

This synthesis is carried out by a process including the steps:
a: acetylation of $2^3$PCP obtained in Example 1 by means of a Friedel and Crafts type reaction;
b: reduction of the acetylated derivative obtained;
c: dehydration of the alcohol formed which results in the desired vinyl derivative.

a: acetylation

Operation is as indicated by Tabushi, p.8452, in the aforesaid reference.

A mixture of 500 mg of $2^3$PCP and of 428 mg of aluminium chloride $AlCl_3$ in 4 ml of carbon disulfide $CS_2$ is formed. This mixture is subjected to stirring and, drop by drop, in one hour, is added a solution of 158 mg of acetic anhydride $(CH_3CO)_2O$ in 1 ml of $CS_2$.

After an additional stirring for about two hours, the reaction solution is poured onto a mixture of ice and hydrochloric acid HCl. It is extracted with chloroform $CHCl_3$ and the chloroform extract is washed with water, then a saturated solution of sodium bicarbonate $NaHCO_3$ and finally with a saturated solution of sodium chloride NaCl.

After drying and concentration of the solution, the reaction mixture is subjected to chromatography on a silica gel column. It is first eluted with petroleum ether and then with benzene. By evaporation of the fractions eluted with the benzene, the desired derivative of PCP substituted by an acetyl group is recovered, with MP 80°-81° C.

b: reduction

The acetyl group is converted into a primary alcohol functional group by operating according to conventional techniques, and notably by reacting the acetyl derivative with a double hydride such as sodium borohydride, or mixed Al or Li hydride. The corresponding alcohol formed is collected.

c: dehydration

The alcohol obtained is subjected to a dehydration reaction by operating, for example, in an acid medium according to the usual operational methods of alkene synthesis, notably with $KHSO_4$.

EXAMPLE 3

Preparation of poly-vinyl-$2^3$PCP including the unit

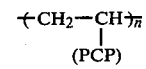

The vinyl monomer such as obtained according to Example 2 is subjected to a radical polymerisation reaction. According to the usual techniques in this field, such as those used for preparing polystyrene, free radicals are produced by means of initiators such as peroxides or azo compounds subject to thermal decomposition.

EXAMPLE 4

Preparation of PCP derivatives in which the aromatic rings are linked by ethylene groups —CH=CH—. By operating according to one of the methods of general synthesis of alkenes, there is utilised, as a starting material, a derivative of PCP including monohalogen connecting links, for example, monobrominated compounds and corresponding therefore to the formula —CH$_2$—CHBr—, and it is subjected to a dehydrohalogenation reaction in an alcoholic medium in the presence of a strong base such as potash.

EXAMPLE 5

Preparation of derivatives of PCP including connecting links of the ester type corresponding therefore to the formula —CO—O—.

Acetylsalicylic acid is heated to 200° C. approximately, which leads to paraacetoxybenzoic acid.

By dry heating, this acid is trimerised forming the desired ester with the elimination of acetic acid. This ester is separated from the reaction mixture by liquid phase chromatography under high pressure. The technique of Wilson Baker in J.-Chem. Soc. 1951, p.201 is also advantageously used.

EXAMPLE 6

Preparation of derivatives of PCP in which the aromatic rings are connected by amide groups of the formula —CO—NH— or —CO—N—R$_7$.

Operation is as in Example 5 but starting from p-acetamido-benzoic acid, the acetamide group being, if necessary, substituted by R$_7$.

EXAMPLE 7

Preparation of derivatives of PCP in which the aromatic rings are connected by ether groups —CH$_2$—O—.

Procedure is as in Example 5 but starting from p-chloromethylphenol and operating in a basic medium. The condensation of the phenol derivative is accompanied by elimination of hydrochloric acid.

EXAMPLE 8

Preparation of tetrakis [1,1,1,1,] paracyclophane or $1^4$-PCP of the formula

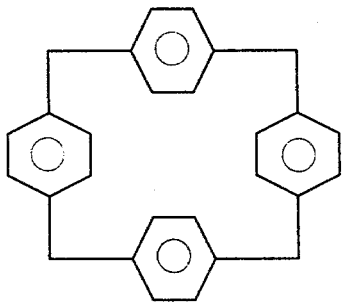

A p-halogenomethyl-benzene, notably benzyl chloride is subjected to a Friedel and Crafts type reaction, operating in a highly diluted medium in a chlorinated inert solvent, such as dichlorobenzene, or methylene chloride, in the presence of aluminium trichloride $AlCl_3$ and/or boron trifluoride $BF_3$. By elimination of hydrochloric acid, the desired condensation into a tetramer is obtained. In a modification, p-xylylene chloride is reacted with benzene.

EXAMPLE 9

Preparation of PCP derivatives in which the aromatic rings are connected by silanol groups

To obtain this type of compound, a phenolsilanol derivative of the type

HO-C$_6$H$_4$-Si(R$_{13}$,R$_{14}$)-OH.

is condensed in an acid or basic medium.

EXAMPLE 10

Preparation of PCP derivatives in which the aromatic rings are connected by a disulfide bridge.

Procedure is according to conventional techniques oxidising the P, P'-thiol HS-C$_6$H$_4$-SH by means of a gentle oxidising agent such as halogens, $H_2SO_4$ or the like.

EXAMPLE 11

Preparation of PCP derivatives including

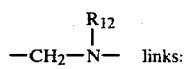

The condensation of p-amino, p' chloromethyl molecules of the $R_{12}NH$-$C_6H_4$-$CH_2Cl$ type in an inert solvent is carried out.

EXAMPLE 12

Preparation of PCP derivatives including —CH═CH— links. In a modification of the method described in Example 4, said PCP's are prepared by operating according to the method described by D. J. CRAM and K. C. DEWHIRST in J.A.C.S. 1969-81 p. 5963. 3.1 g of $2^3$PCP and 10.8 g of N-bromosuccinimide are mixed in 300 ml of $CCl_4$. A small amount of benzoyl peroxide is added, it is stirring and heated under reflux for about 14 h. The mixture is filtered, concentrated, then diluted with pentane. 7.2 g of crude product are recovered MP 250°-280° C. (yield 91%). For the analysis, the product is chromatographed and it is recrystallised in a mixture of benzene and of hexane, which gives an isomer of MP (decomp), 303° C. 4.5 g of hexabrominated derivative, 20 g of zinc activated with $NH_4Cl$ and 600 ml of ethanol are mixed. The mixture is brought to reflux under nitrogen for about 14 h, then filtered to eliminate the zinc.

The solid recovered is chromatographed on a neutral alumina column using pentane as a eluent. 820 mg of product of MP 128°-131° C. are obtained (yield 47%). A purification by repeated crystallisation in an ethanol-water mixture gives a product of MP 136°-136.8° C.

EXAMPLE 13

The general operational method used is the following: a solution of $2^3$PCP in an organic solvent is saturated with hydrogen under pre-determined conditions of temperature and pressure. The solution is then rapidly frozen to 77K and the gaseous hydrogen of the enclosure is evacuated under primary vacuum ($10^{-1}$ to $10^{-3}$ torr).

After reheating to ordinary temperature, the dissolved $H_2$ is extracted by evaporation of the solvent and then by condensation in a cold trap. The volume of gas extracted is measured by means of a Töpler pump operating with mercury and a gas burette. In the tests whose results are reported below, there is used as solvent, a solvent common both to the hydrogen and to the PCP derivatives such as dichloromethane $CH_2Cl_2$.

In the following Table, the measurements of gas extracted in the presence of a known amount of $2^3$PCP are compared with those obtained, on the one hand, by means of the solvent alone, and on the other hand, of a solution of the same molarity of the non-cyclic homolog of $2^3$PCP namely 1,4 bis(p-tolylethyl)-benzene or BTS. These measurements expressed in cm$^3$, brought to normal conditions of temperature and pressure, are given as a function of the nature of the solution used and of the saturation conditions utilised. In this regard there is indicated in each case the total volume of hydrogen adsorbed by the solution and the calculated volume corresponding to the hydrogen trapped by the PCP macrocycle, this volume being obtained by difference with the control experiment. The ratio of complexation or of filling of the cavities is also recorded and corresponds to the ratio of the number of molecules of gas trapped or complexed to the number of molecules of macrocycle present in solution.

| Nature of the solution | | | Saturation conditions | | | V (cm³) | | Complexation ratio |
|---|---|---|---|---|---|---|---|---|
| V(ml) $CH_2Cl_2$ | Mass $2^3PCP$ | (mg) BTB | P (bars) | T(°C.) | t(min) | $H_2$ measured | trapped | $0 \times 100$ |
| 1 | 0 | 0 | 50.45 | 24 | 120 | 2.31 | — | — |
| 1 | 0 | 88.47 | 50.43 | 25 | 60 | 2.48 | — | — |
| 1 | 0 | 88.47 | 50.49 | 22 | 60 | 2.53 | — | — |
| 1 | 58.5 | 0 | 10.50 | 21.5 | 60 | 0.93 | 0.41 | 9.8 |
| 1 | 89.28 | 0 | 20.53 | 20 | 60 | 1.65 | 0.64 | 10 |
| 1 | 58.5 | 0 | 30.47 | 23 | 60 | 2.41 | 0.90 | 21.4 |
| 1 | 58.5 | 0 | 50.47 | 23 | 60 | 3.58 | 1.08 | 25.6 |

The examination of the results of this Table demonstrates the inclusion of $H_2$ in the housings of the $2^3PCP$ in solution and this advantageously at temperatures of the order of ambient temperature and under easily accessible pressures of about 10 to 15 bars. The comparison of the results obtained with the $2^3PCP$ and its linear homolog is also interesting and establishes that the adsorption of hydrogen is effected by penetration of the gas into the intramolecular cavity of the PCP.

We claim:

1. A method of retaining gases in the intramolecular cavity of a gas adsorption agent comprising at least one paracyclophane (or PCP) derivative, constituted by cyclic oligomers formed of oligomer-units which are interlinked so as to define a rigid structure with a substantially cylindrical intramolecular cavity, the dimensions of the cross-section of said cavity corresponding substantially to those of the one or more types of gas molecules that it is desired to insert therein, the rigidity of said structure being such that the rotary movements of the atoms which constitute said units cannot result in substantial variations in the volume of said cavity up to a temperature of the order of 250° C., which comprises:

(a) contacting a medium comprising the gas to be adsorbed whose molecules have a dimension substantially similar to those of the internal space of said gas adsorption agent with the aforesaid gas adsorption agent;

(b) permitting said gas adsorption agent to adsorb said gas; and (c) separating said gas adsorption agent containing said adsorbed gas from the medium previously containing said adsorbed gas.

2. A method according to claim 1, wherein the rigidity of the structure of the gas adsorption agent is such that the variations in the cavity cross-section, up to a temperature of about 250° C., do not exceed ±10% of said cavity cross-section.

3. A method according to claim 1, wherein the gas adsorption agent comprises at least one PCP trimer formed from three units, which units can differ from one another, corresponding to the formula RX, in which R is an aromatic cyclic compound with six link chains substituted at each of the para positions by X, this cyclic compound being selected from the group consisting of phenylene, pyridinyl and the pyrimidyl nitrogen aromatic radical, provided that the one or more nitrogen atoms do not occupy the positions substituted at para by X; and X is a linear link with two elements, selected from the group consisting of the radicals

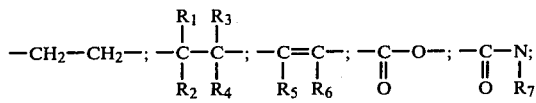

-continued

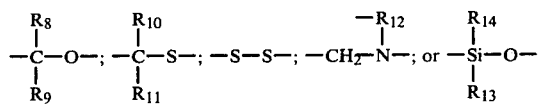

$R_1$ to $R_4$, identical or different from one another, representing a $C_nH_{2n+1}$ group with $0 < n \leq 4$ or a halogen atom selected from among F, Cl or Br, $R_5$ to $R_{14}$ being able to represent, in addition to the meanings given for $R_1$ to $R_4$, a hydrogen atom.

4. A method, according to claim 3, wherein the gas adsorption agent comprises at least one PCP trimer in which X is a —$CH_2$—$CH_2$— link chain.

5. A method according to claim 3, wherein the gas adsorption agent comprises at least one PCP trimer in which X is a functional ester group.

6. A method, according to claim 3, wherein the gas adsorption agent has at least one of the aromatic rings substituted by at least one element selected from the group consisting of halogens, in particular F, Cl and Br; acid groups such as —COOH or —$SO_3H$; ammonium cations of the —$N(R_{15})_3^+$ type, $R_{15}$ representing a $C_{n'}H_{2n'+1}$ radical with $0 \leq n' \leq 2$; or ethylenically unsaturated groups.

7. A method according to claim 6, wherein said ethylenically unsaturated group of the gas adsorption agent is a vinyl group.

8. A method according to claim 3, wherein the gas adsorption agent comprises a PCP molecule attached to a polymer chain.

9. A method according to claim 8, wherein the polymer chain of the gas adsorption agent is of the poly (p-vinyl-PCP) type.

10. A method according to claim 8, wherein the polymer chain of the gas adsorption agent comprises a macromolecular framework or pattern on which the PCP units are fixed.

11. A method according to claim 3, wherein the gas retained is hydrogen.

12. A method of retaining hydrogen according to claim 11, wherein the temperatures utilized are temperatures near ambient temperature, and the pressure range utilized is 5 to 100 bars.

13. A method according to claim 12, wherein the pressure range is from 5 to 50 bars.

14. A method according to claim 11 for the purification and concentration of hydrogen, wherein a phase enclosing an effective amount of at least one of said gas adsorption agents is contacted with a gaseous or liquid phase including hydrogen in admixture with $O_2$, $N_2$ or $H_2O$.

15. A method according to claim 11, wherein an effective amount of at least one of said gas adsorption agents is utilized to protect a storage compound of hydrogen, such as a metallic hydride, from the action of oxygen.

16. A method according to claim 11, wherein the gas adsorption agent is utilized in an electrochemical process employing hydrogen for recovering at least part of a hydrogen electrode.

17. A method according to claim 11, wherein said gas adsorption agent is applied, in the solid state, selected from bead, granule, and membrane form, said gas adsorption agent being dispersed in an amorphous phase of a macromolecular material.

18. A method according to claim 11, wherein said gas adsorption agent is utilized as a dispersion or solution in a liquid.

19. A method according to claim 18, wherein said gas adsorption agent is utilized in a conventional membrane material.

20. A method according to claim 1, wherein the gas adsorption agent includes at least one cyclic tetramer formed from oligomer-units R-Y in which R is an aromatic cyclic compound with 6 links, substituted at each of the para positions by Y, this cyclic compound being selected from the group consisting of phenylene, pyridinyl or pyrimidyl nitrogen aromatic radical, provided that the one or more nitrogen atoms do not occupy the positions substituted at para by Y; and Y is a link with an element selected from the group consisting of

in which $R_5$ and $R_6$ are identical or different from one another, representing a $C_nH_{2n+1}$ group with $0 \leq n \leq 4$ or a halogen atom selected from among F, Cl or Br; or a hydrogen atom;

—O— or —S—.

21. A method according to claim 20 wherein the molecules of the gas retained occupy a volume greater than that occupied by molecules of hydrogen.

22. A method according to claim 21 wherein the gas retained is $O_2$, $N_2$, CO or $H_2O$.

23. An electrode formed of a porous metal or other conventionally used materials which additionally comprises a gas adsorption agent, said gas adsorption agent comprising at least one paracyclophane (or PCP) derivative, constituted by cyclic oligomers formed of oligomer-units which are interlinked so as to define a rigid structure with a substantially cylindrical intramolecular cavity, the dimensions of the cross-section of said cavity corresponding substantially to those of the one or more types of gas molecules that it is desired to insert therein, the rigidity of said structure being such that the rotary movements of the atoms which constitute said units cannot result in substantial variations in the volume of said cavity up to a temperature of the order of 250° C.

24. An electrode according to claim 23 wherein the gas adsorption agent is applied in film form to said electrode.

* * * * *

UNITED STATES PATENT AND TRADEMARK OFFICE
CERTIFICATE OF CORRECTION

PATENT NO. : 4,359,327
DATED : November 16, 1982
INVENTOR(S) : M. Armand

It is certified that error appears in the above-identified patent and that said Letters Patent are hereby corrected as shown below:

Column 3, lines 3 and 5 delete "A" each instance and insert --$A°$-- each instance.

Column 7, line 44 delete "428" insert --438--.

Column 11, line 14 delete "stirring" insert --stirred--.

Signed and Sealed this

Nineteenth Day of April 1983

[SEAL]

Attest:

Attesting Officer

GERALD J. MOSSINGHOFF

Commissioner of Patents and Trademarks